United States Patent [19]

Walsh et al.

[11] Patent Number: 5,925,619
[45] Date of Patent: Jul. 20, 1999

[54] FORMULATION FOR PEPTIDE RELEASE

[75] Inventors: John D. Walsh, Curl Curl; Timothy E. Trigg, Warrawee, both of Australia

[73] Assignee: Peptech Limited, NSW, Australia

[21] Appl. No.: 08/981,285

[22] PCT Filed: Jun. 20, 1996

[86] PCT No.: PCT/AU96/00370

§ 371 Date: Dec. 19, 1997

§ 102(e) Date: Dec. 19, 1997

[87] PCT Pub. No.: WO97/00693

PCT Pub. Date: Jan. 9, 1997

[30] Foreign Application Priority Data

Jun. 20, 1995 [AU] Australia .................... PN3667

[51] Int. Cl.$^6$ .............................. A61D 19/00; A61D 7/00
[52] U.S. Cl. ........................ 514/15; 514/3; 514/8; 514/12; 514/13; 514/14; 514/15; 424/422; 424/423; 424/425; 424/426
[58] Field of Search .................. 514/8, 12, 13–15, 514/3, 21; 424/177, 422, 423, 425, 426

[56] References Cited

U.S. PATENT DOCUMENTS 3,917,825 11/1975 Matsuzawa et al. .
5,538,739 7/1996 Bodmer et al. ........................ 424/501

FOREIGN PATENT DOCUMENTS

37929/78 1/1980 Australia .
302582 2/1989 European Pat. Off. .
2052258 1/1981 United Kingdom .
92/18107 10/1992 WIPO .
93/15722 8/1993 WIPO .

OTHER PUBLICATIONS

Journal of Clinical Endocrinolgy and Metabolism, 1991 by The Endocrine Society; Effects of Pitsuitary–Testicular Axis Suppression in Utero and During the Early Neonatal Period With Long–Acting Luteinizing Hormone–Releasing Hormone Analog on Gential Development, Somatic Growth, and Bone Density in Male Cynomolgus Monkeys in the First 6 Months of Life, By Linda Liu et al, pp. 1038–1043.

British Poultry Science, vol. 33, No. 3 1992, (Edinburgh, Scotland), A.J. Tilbrook et al, "Short–term reduction in Egg Production in Laying Hens Treated With an Agonist of GnRH". pp. 621–638.

Journal of Animal Science, vol. 74, No. 1, 1996 (Champaign, Illinois, U.S.A.), D'Occhio, M.J. et al "Controlled Reversible Suppression of Beef Heifers and Cows using Agonists of Gonadotrophin–Releasing Hormone", pp. 218–225, see especially p. 233.

Biology of Reproduction, vol. 42, No. 1, 1996(champaign, Illinoise, U.S.A.), D'Occhio, M.J. et al "Characteristics Hormones (LH) and Testosterone Secretion, Pituitary Responses to LH–Releasing Hormone (LHRH), and Reproductive Function in Young Bulls Receiving the LHRH Agonist Deslorelin: Effect of castration on LH responses to LRRH" pp. 45–52, See especially p. 46.

Stedman's Medical Dictionary, 25$^{th}$Ed., Williams & Wilkins, Baltimore, USA p. 1472.

*Primary Examiner*—F. T. Moezie
*Attorney, Agent, or Firm*—Nixon & Vanderhye

[57] ABSTRACT

A pharmaceutical or veterinary formulation comprising deslorelin and an excipient is provided which releases in vitro deslorelin into phosphate buffered saline at 370° C. at a rate of about 2–80 μg/day for at least 200 days. The formulation may be used for prevention of reproductive function, particularly in dogs and cats, and for the treatment particularly in humans, of prostate and breast cancer and other diseases and conditions where suppression of testosterone or estradiol levels is beneficial.

9 Claims, 21 Drawing Sheets

FORMULATION FOR PEPTIDE RELEASE

The present invention relates to pharmaceutical and veterinary formulations for the sustained release of deslorelin which is an agonist of the peptide gonadotropin releasing hormone (GnRH). Uses of the formulations include prevention of reproductive function, particularly in dogs and cats, and treatment, particularly in humans, of prostate and breast cancer and other diseases or conditions where suppression of testosterone or estradiol levels is beneficial.

BACKGROUND OF THE INVENTION

Uncontrolled reproduction in domestic pets is a world wide problem. In less developed countries, reproduction of domestic cats and dogs is relatively uncontrolled. Sporadic programs of work exist aimed at controlling reproduction in these animals by surgical castration. In the more developed countries, reproduction is controlled more by ovarectomy in females and in some cases, by orchidectomy in males, or by physically locking away animals to prevent mating.

Surgical techniques, no matter how minor, carry some risk. Many pet owners are also loathe to have their animal surgically modified and will tolerate the problems of uncontrolled reproduction and associated behaviour. To remove the ability to reproduce from domestic pets without the use of surgery and without resorting to lengthy kennelling procedures has been an objective of the small animal research industry for some years. Drugs which are currently available for this process, are steroid-based drugs. They produce unpleasant side effects, particularly after lengthy use, and they are not widely used.

The peptide gonadotrophin releasing hormone (GnRH) has been the subject of intensive research for many years. It is a hypothalamic decapeptide which is synthesised and stored in neurosecretory cells of the medial basal hypothalamus. The releasing hormone is released in a pulsatile manner into the hypophysial portal circulation and is transported to the anterior pituitary. Here, it regulates the secretion of the gonadotrophins, luteinising hormone (LH) and follicle stimulating hormone (FSH), into the systemic circulation. Thus, GnRH is a humoral link between the neural and endocrine components of reproductive function (for review see Conn P. M. (ed) 1996 Gonadotropin-releasing hormone Endocrine Review 7:1). GnRH binds to a single class of receptors on gonadotrope cells. Prolonged exposure of these cells to the GnRH results in loss of responsiveness to the hormone, through receptor alteration (reviewed in Hazum E. and Conn P. M. (1988) Endocrine Review 9:379–856). The outcome of down-regulation of responsiveness to GnRH is suppression of circulating levels of gonadotropins and sex hormones. This has the consequence of suppressing reproductive function and other processes affected by sex hormone levels.

For many years, researchers have tried to develop a commercial vaccine, based on forming antibodies to GnRH, to cut this hormone axis and hence act as a contraceptive. The present applicants have commercialised such a vaccine; however, the developed technology is not suitable for contraception in pets. This lack of suitability is due to the biological variation of response in individual pets to a vaccine and the lack of predictability of the length of effect of the vaccine.

It is generally accepted in the marketplace that for a pet contraceptive to be successful, it would be preferably efficacious in all treated animals and its length of response time would be predictable. This response should preferably either be for six or twelve months. Reversibility of the effect would be an additional desirable benefit.

In 1987, Brian Vickery from Louisiana (Vickery, B. H. and Nestor, J. J. (1987) In LHRH and its Analogues, Part 2, p 517–543), demonstrated that overdosing dogs/bitches with the superagonist of GnRH, nafarelin, shut down reproductive function for a variable period of three to eighteen months. The difficulties facing product development in this area have been:

(i) to have available a source of GnRH, or an agonist, at a cost effective price; and (ii) to have a cost-effective delivery system for a peptide which releases at a controlled rate over six to twelve months, at a rate and dose that will shut down animals predictably and reliably for six or twelve months.

The present applicants have developed a formulation comprising deslorelin as the active agent which, when administered to animals, prevents reproductive function over an extended and predictable period of time. The formulation also allows the restoration of reproductive function following termination of administration. Whilst the formulation is particularly described in relation to dogs, it is believed that the formulation will be useful in other animals such as humans.

In addition, the use of GnRH analogues, including deslorelin, for the suppression of hormonie levels in humans is well documented. Van Leusden H. A. I. M. (Gynecol Endocrinol 8 (1994) 215–222) has reviewed the use of a variety of GnRH agonist peptides for suppression of estradiol levels in female patients and use for the treatment of endometriosis and leiomyoma. From a survey of a large body of published work, these authors concluded that many GnRH analogues, including deslorelin, were effective in suppressing estradiol levels and hence in treating these sex hormone-accelerated conditions provided that the peptide was delivered so as to maintain a constant minimum blood level. The prerequisite for a peptide to be active was the ability to disturb the pulsatile release of endogenous GnRH. This required a constant minimum plasma level (this level was not defined). They suggested that a mode of delivery was more important than minor differences in potency between different GnRH analogues. These authors also concluded that in a suppressed pituitary, the dose of GnRH analogue needed to maintain suppression gradually decreased with the duration of treatment (also explored in Sandow J. and Donnez T. (1990) in Brosens I., Jacobs H. S. and Rennebaum B. (eds) LHRH analogues in Gynaecology pp 17–31 Camnforth: Parthenon Publishing).

Similarly, the use of GnRH agonists including deslorelin, in the treatment of sex hormone dependent tumours, including breast cancer and prostate cancer, has been described. Redding et al, (1984) Proc Natl Acad Sci U.S.A. 81 5845–5848 described the use of a GnRH analogue [D Trp$^6$] LH-RH for suppression of prostate cancer in rats and demonstrated that a microencapsulated form of the peptide, delivering a controlled dose over a, 30 day period was more effective in suppressing serum testosterone levels and prostate tumour weight than daily subcutaneous administration of equivalent or double doses of the free peptide. The value of this analogue in human prostate cancer patients to suppress testosterone levels and show tumour progression has been demonstrated by Parmar H. et al (1985). The Lancet Nov. 30, 1201–1205. This one month depot injection of a GnRH agonist has now been registered for use and tested and used widely in the treatment of breast, ovarian and prostate cancer, endometriosis, myoma and in precocious puberty in children, as have other GnRH agonists. (Nelson J. R. and Corson S. L. (1993) Fertil Steril 59:441–3; Paul D., Conte F. A., Grumbach, M. M. and Kaplan S. L. (1995) J Clin Endocrin Metab 80:546–551).

A three month depot preparation of a GnRH agonist has also been described (Okada H., Doken Y., Ogawa Y. and Toguchi H. (1994) Pharm Res, (U.S.) 11:1199–1203.). Linear drug release from the injected microspheres was obtained with persistent suppression of serum LH, FSH (rats) and testosterone (rats and dogs) for over 16 weeks. Doses of GnRH analogues used to suppress sex hormone levels in males and females are the same (e.g. Plosker, G. L. and Brogden, R. V. (1994) Drugs Vol. 48, pages 930–967). Thus, the demonstration of suppression of sex hormone levels in one sex is predictive of similar suppression in the other sex.

Accordingly, the abovementioned deslorelin formulation developed by the present applicants, is also useful for treating a range of hormone dependent diseases and conditions in animals (including humans) such as those mentioned above. The formulation offers an improved treatment for these hormone dependent diseases and conditions, by continuing to deliver the GnRH analogue over a period of 12 months or more, thus reducing the need for frequent subcutaneous injections or implant insertions.

SUMMARY OF THE INVENTION

Thus, in a first aspect, the present invention provides a pharmaceutical and/or veterinary formulation comprising about 2–10% (w/w) deslorelin (on an active basis), about 0.5–2.5% (w/w) lecithin and about 85–97.5% (w/w) stearin, the formulation being characterised in that, in vitro, it releases deslorelin into phosphate buffered saline, as hereinafter described, at 37° C. at a rate of about 2–80 µg/day for at least 200 days but preferably for at least 300 days.

In a second aspect the present invention consists in a method of preventing reproductive function in animals for at least 3 months, the method comprising administering to the animal the formulation of the first aspect of the invention.

In a third aspect, the present invention consists in a method of treating a disease or condition for which suppression of sex hormone levels is beneficial in an animal, the method comprising administering to the animal the formulation of the first aspect of the invention.

In a preferred embodiment of the present invention the formulation comprises about 5–10% (w/w) deslorelin (on an active basis), about 0.5–1.5% (w/w) lecithin and about 89–94% (w/w) stearin.

Particularly preferred formulations are;

(I) 94% (w/w) stearin, 5% (w/w) deslorelin (on an active basis) and 1% (w/w) lecithin, and (II) 93% (w/w) stearin, 5% (w/w) deslorelini (on an active basis) and 2% (w/w) lecithin.

In a still further preferred embodiment of the present invention the formulation is for admnistration to humans, or dogs and/or cats.

The formulation will typically exist in the, form of rods which have been extruded. The rods will then be cut into predetermined lengths for implantation in the animal. As will be readily appreciated the length of rod will determine the rate and dose of deslorelin. As opposed to implanting longer rods more than one rod can be implanted in each animal.

The disease or condition referred to in the method of the third aspect of the invention may be any disease or condition wherein reduction of sex hormone (testosterone or estradiol) levels over a prolonged period is beneficial. Examples include prostate cancer, ovarian and breast cancer, benign hormone-dependent disorders such as endomnetriosis, myoma and premenstrual tension, and precocious puberty in children.

Deslorelin is described in U.S. Pat. No. 4,218,439. Deslorelin has the formula [6-D-tryptophan-9-(N-ethyl-L prolinamide)-10-deglycitiamide] or P Glutamine-Histidine-Tryptophan-Serine-Tyrosine-D Tryptophan-Leucine-Arginine-Proline-ethylamide.

Stearin is partially hydrogenated palm oil. Its principle fatty acids are C16:0(45%) and C8:0(53%). Melting point is about 55° C.

Lecithin is phosphatidylcholine. It is a mixture of diglycerides of stearic, palmitic and oleic acids linked to the choline ester of phosphoric acid. Both stearin and lecithin are found in plants and animals.

In order that the nature of the present invention may be more cleaiy understood, preferred forms thereof will now be described with reference to the following non-limiting examples and accompanying figures.

(i) the effect of deslorelin release from formulation II on down-regulating pituitary function, thereby lowering testosterone levels to zero;

(ii) the length of the effect; and (iii) the reversibility of the effect.

Figure 8:
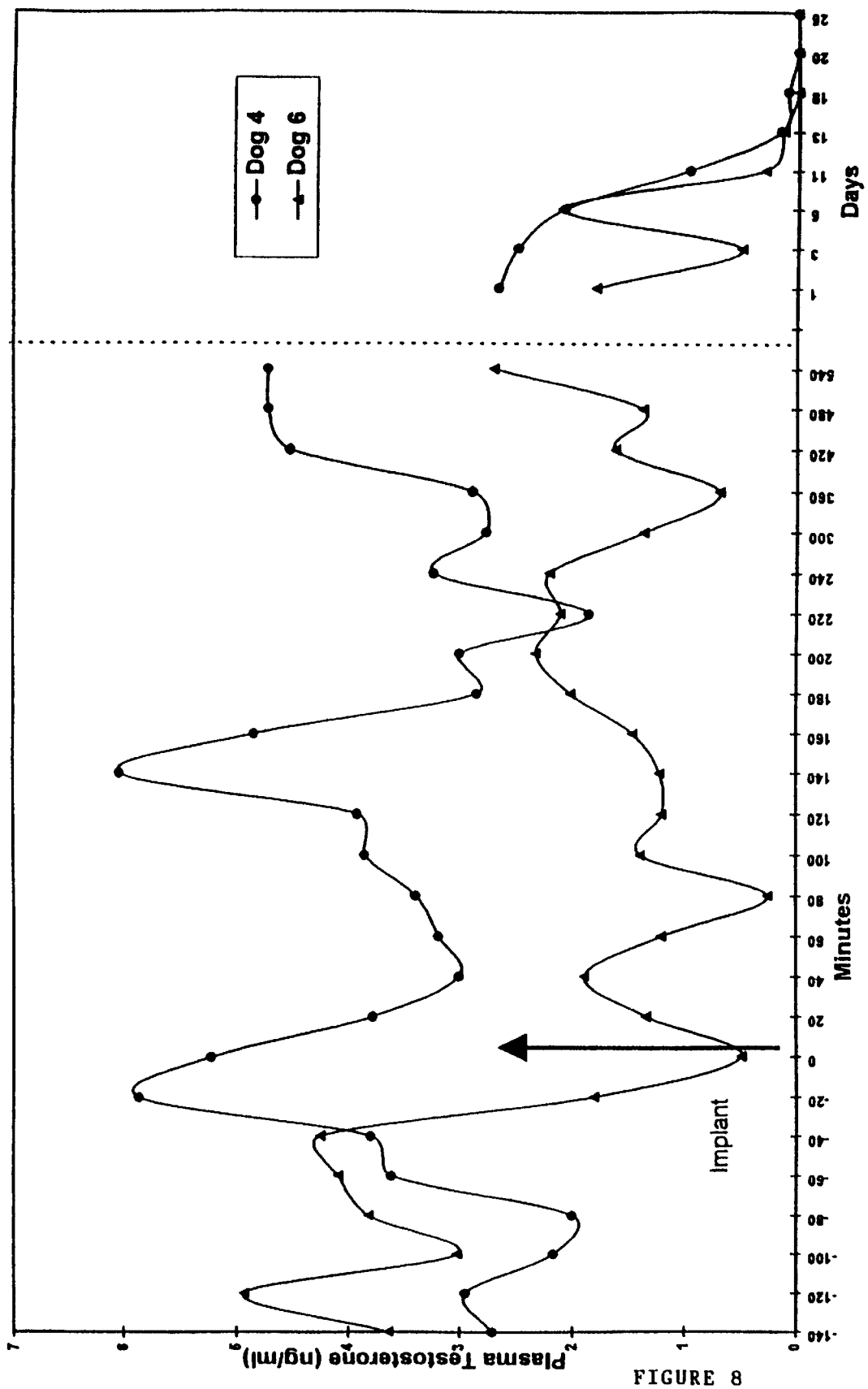
Figure 9A:
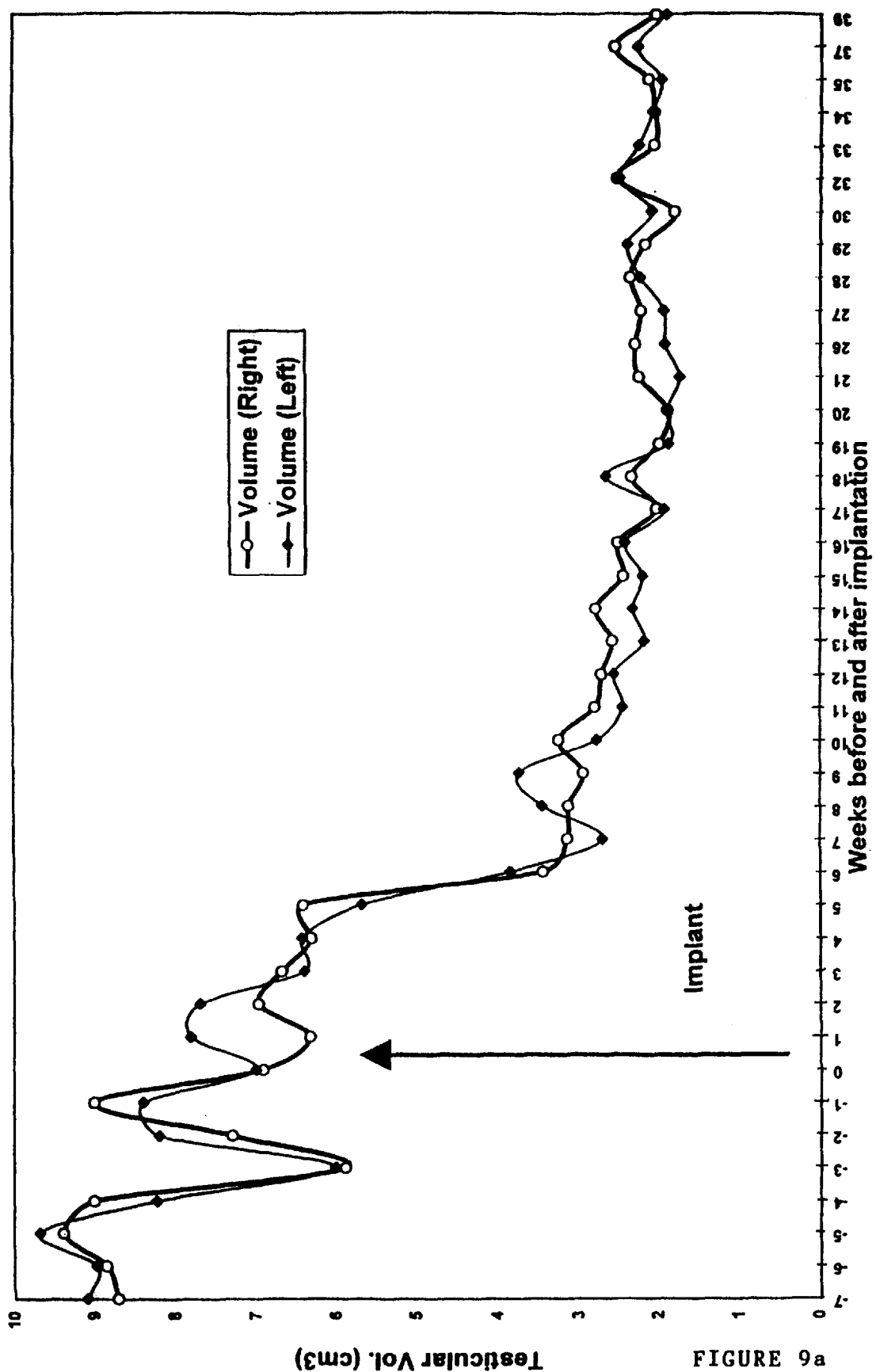
Figure 9B:
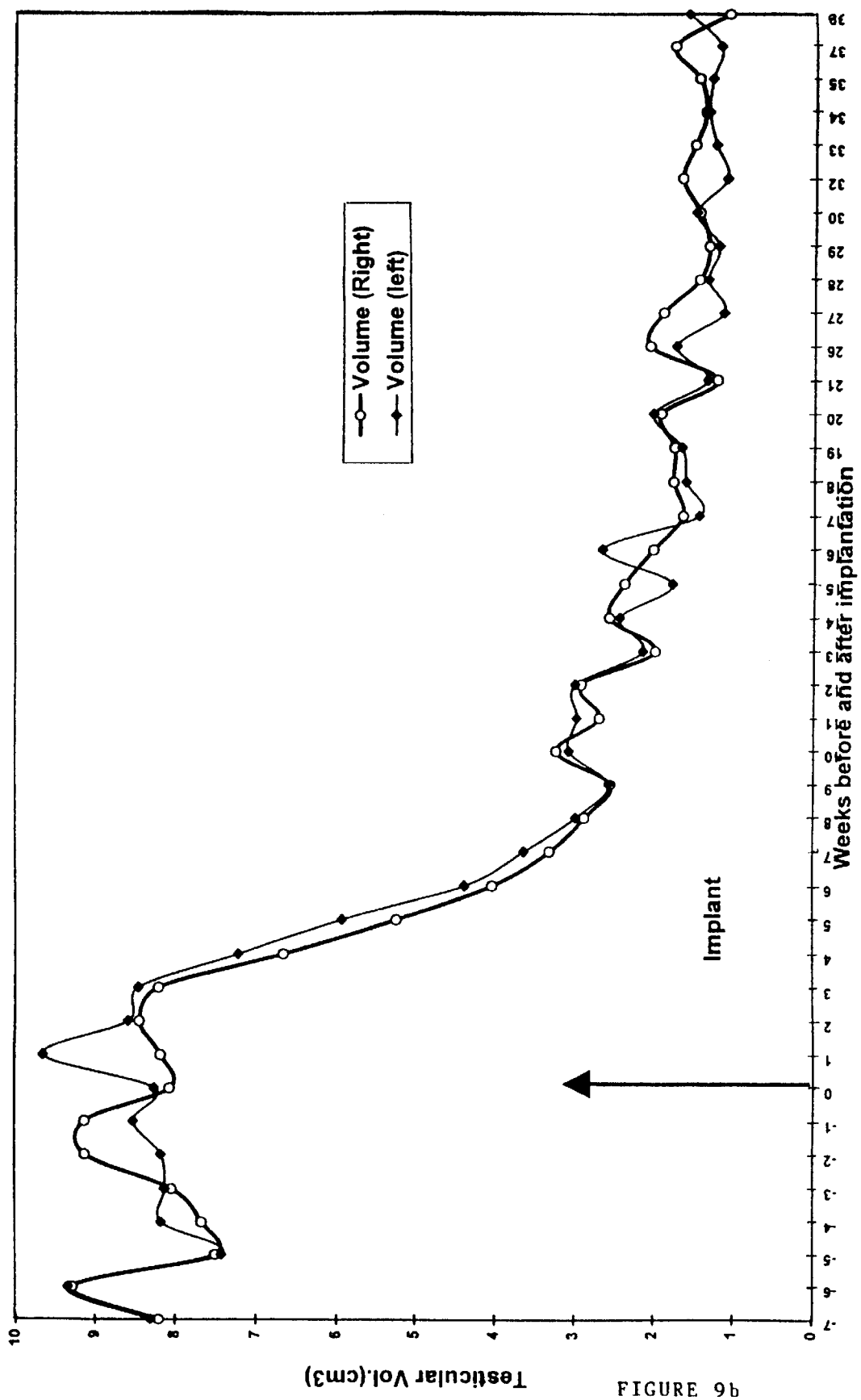
Figure 9C:
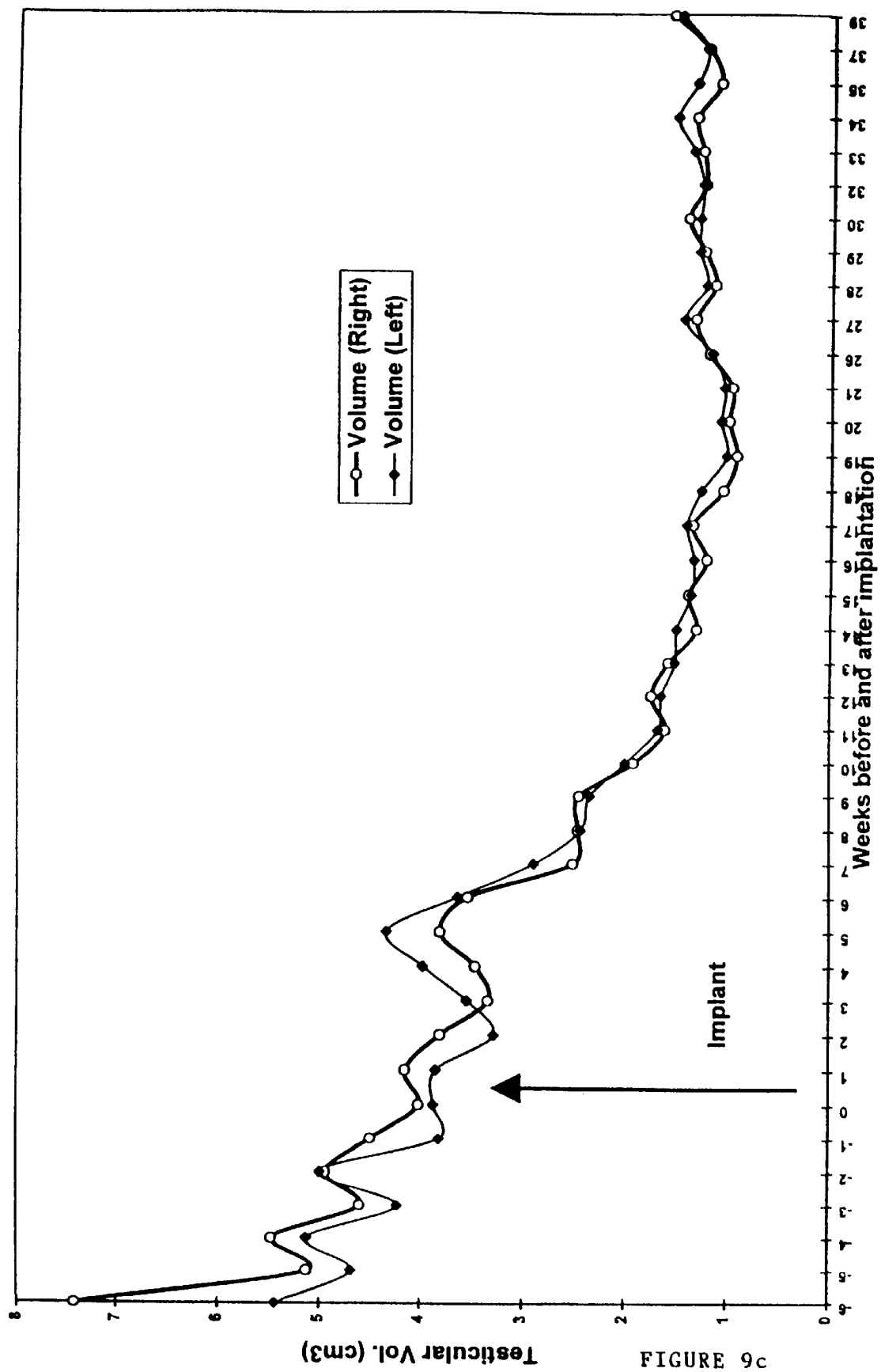
Figure 9D:
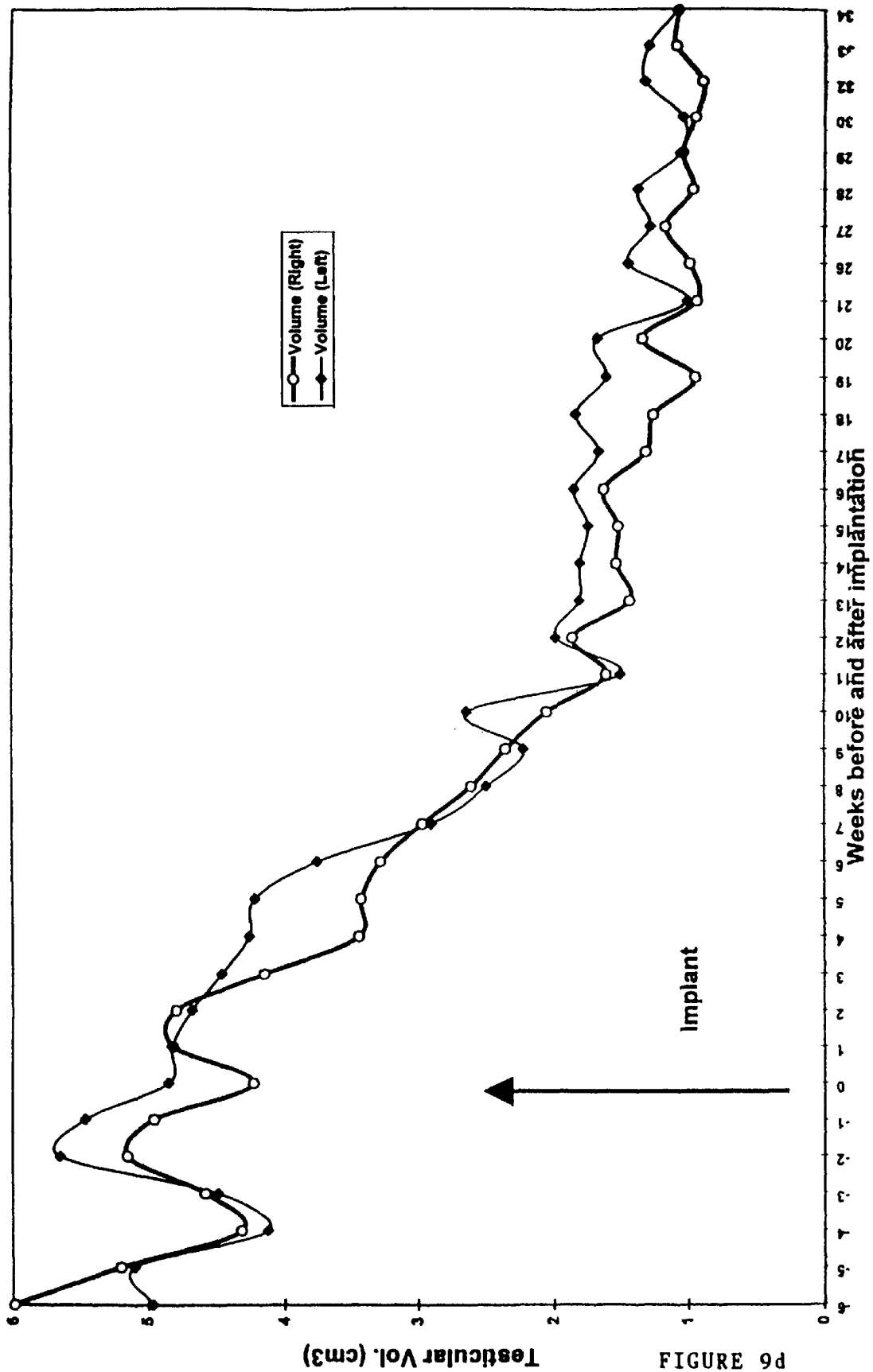
Figure 10A:
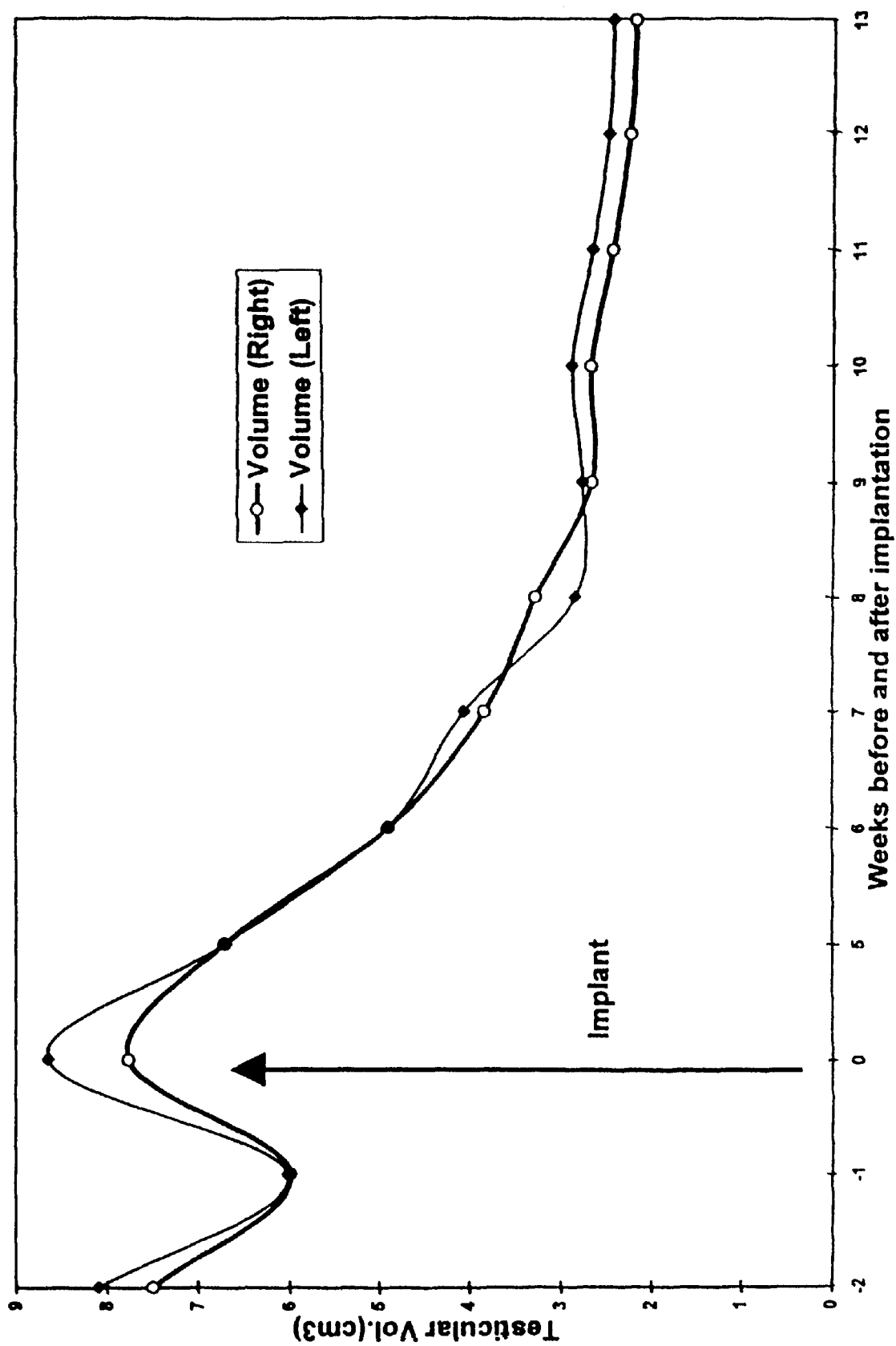
Figure 10B:
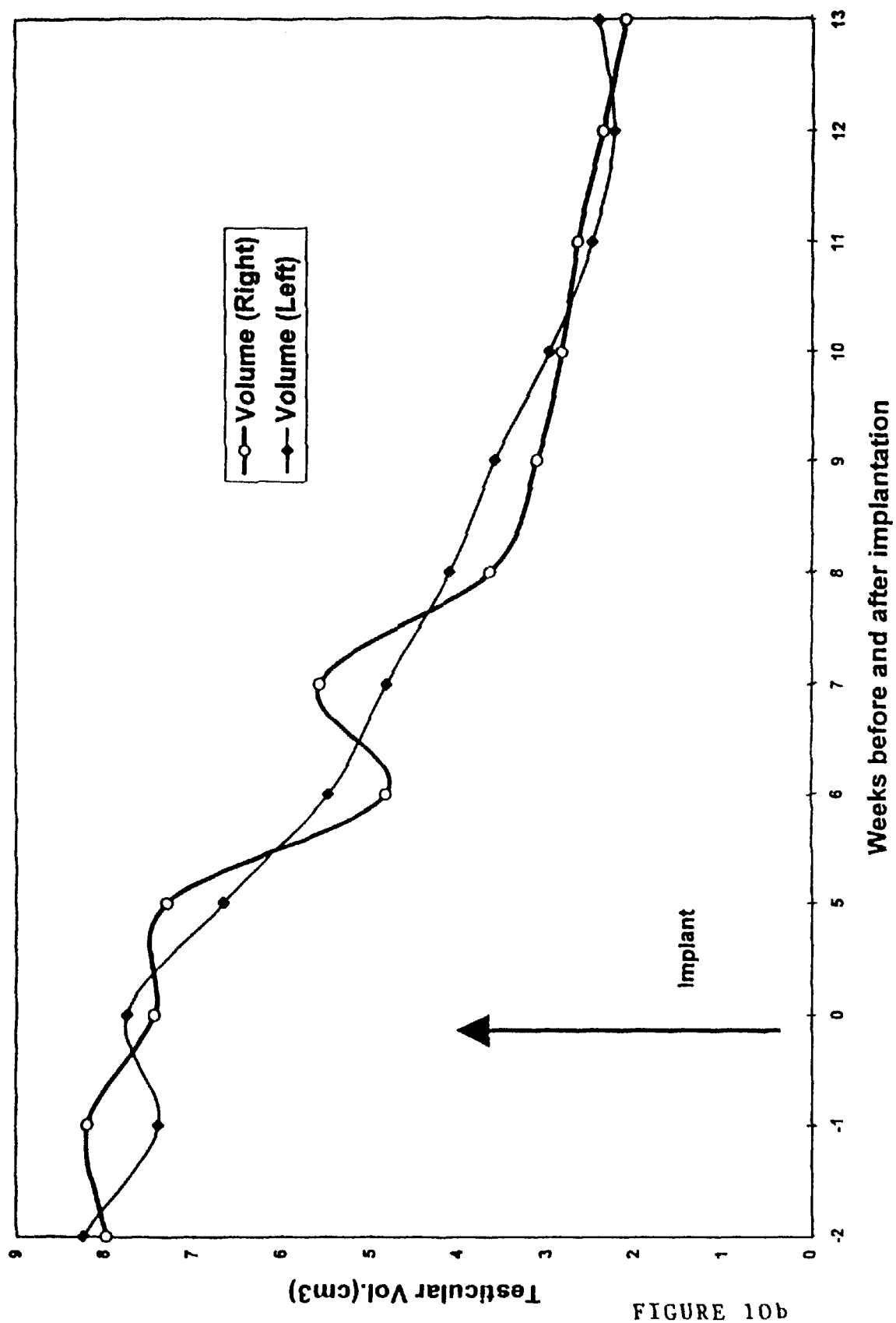
Figure 10C:
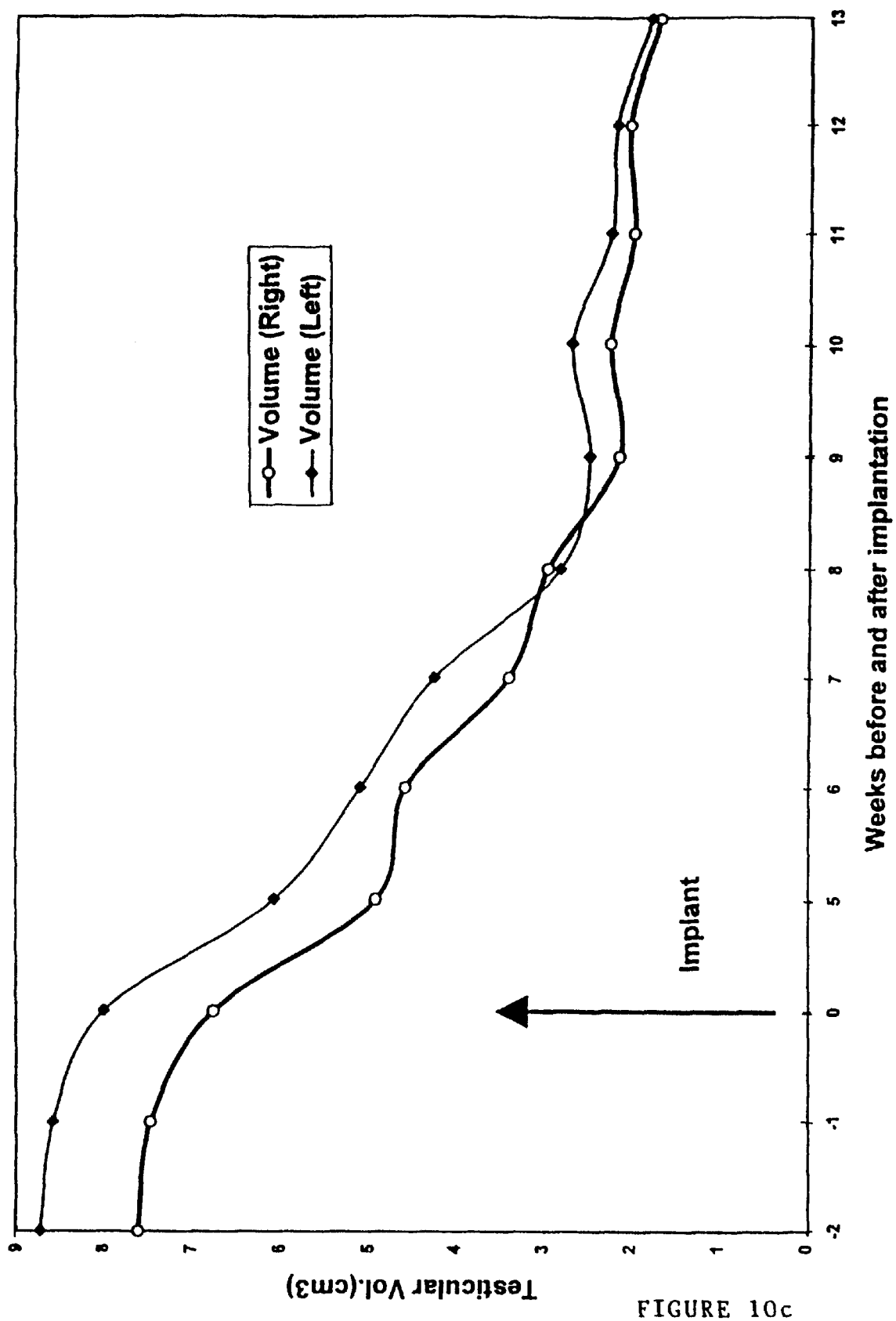
Figure 10D:
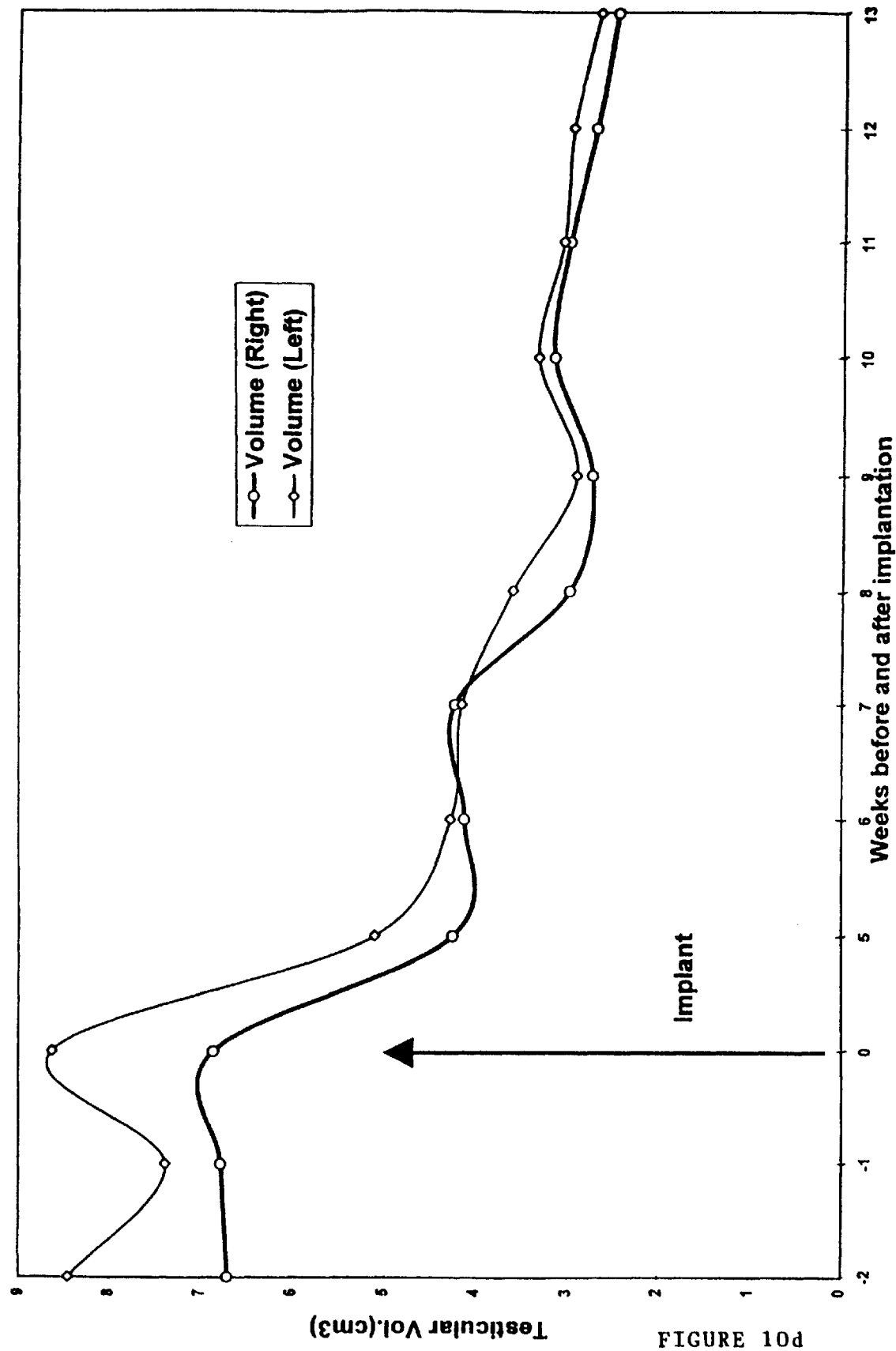

FIG. 8: Provides graphical results of plasma testosterone levels from two dogs implanted with rods of the deslorelin formulation. Reduction in the plasma testosterone levels after 13 days indicates contraception.

FIGS. 9 and 10: Provides graphical results of testicular size data from dogs implanted with the deslorelin formulation up to eight months post implantation. Testicular atrophy is seen in response to pituitary down-regulation.

Figure 11A:
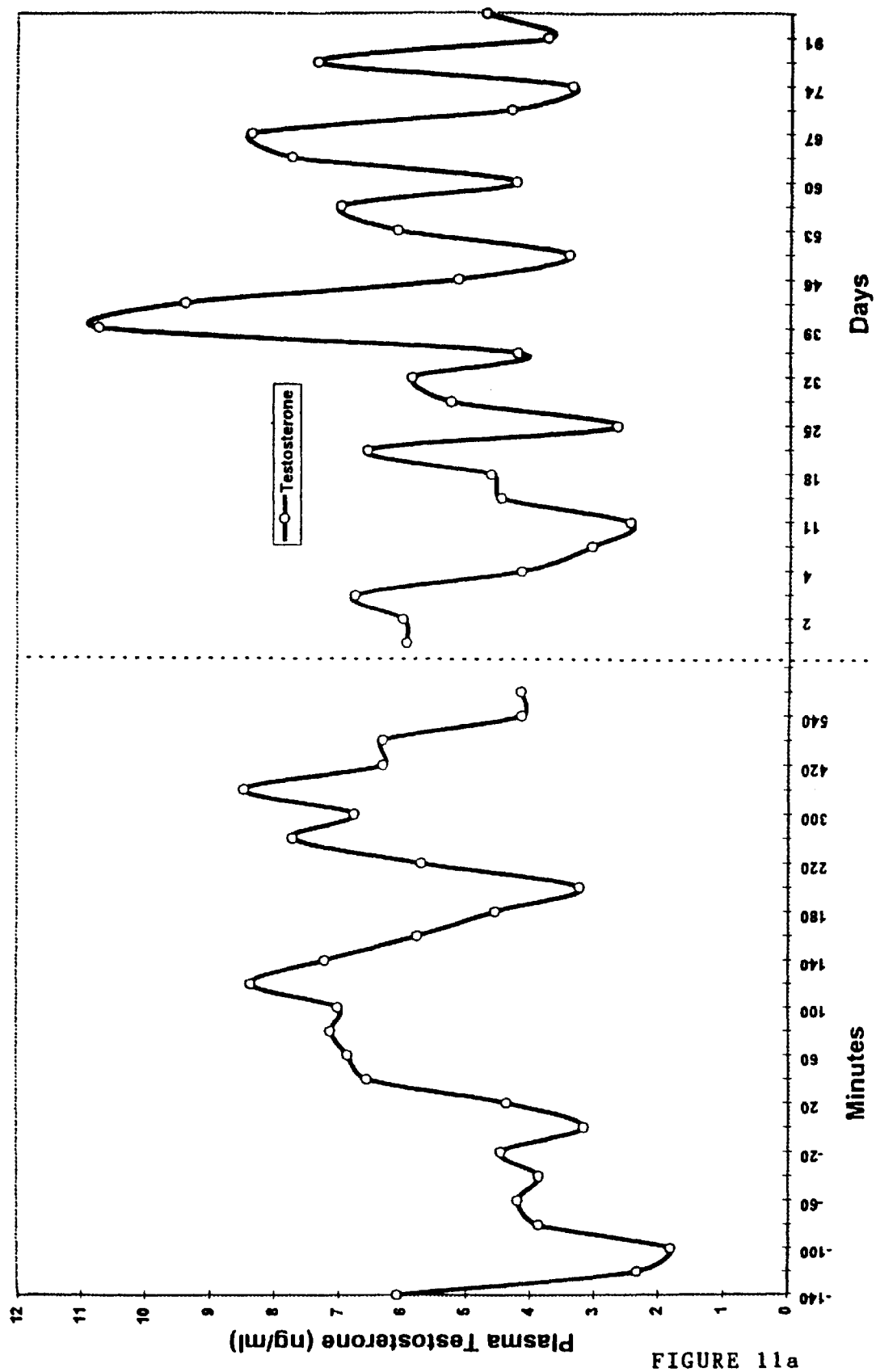
Figure 11B:
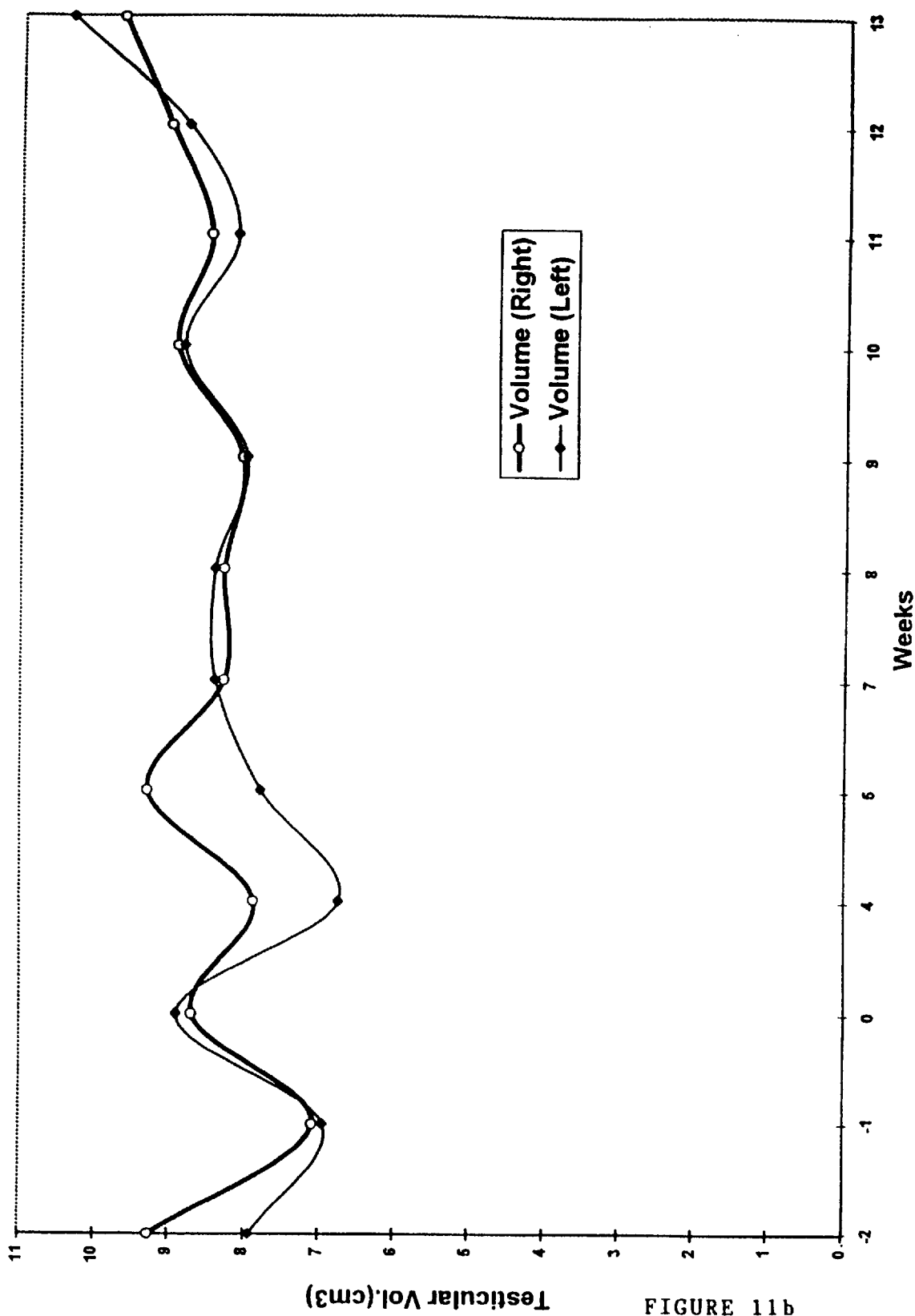
Figure 11C:
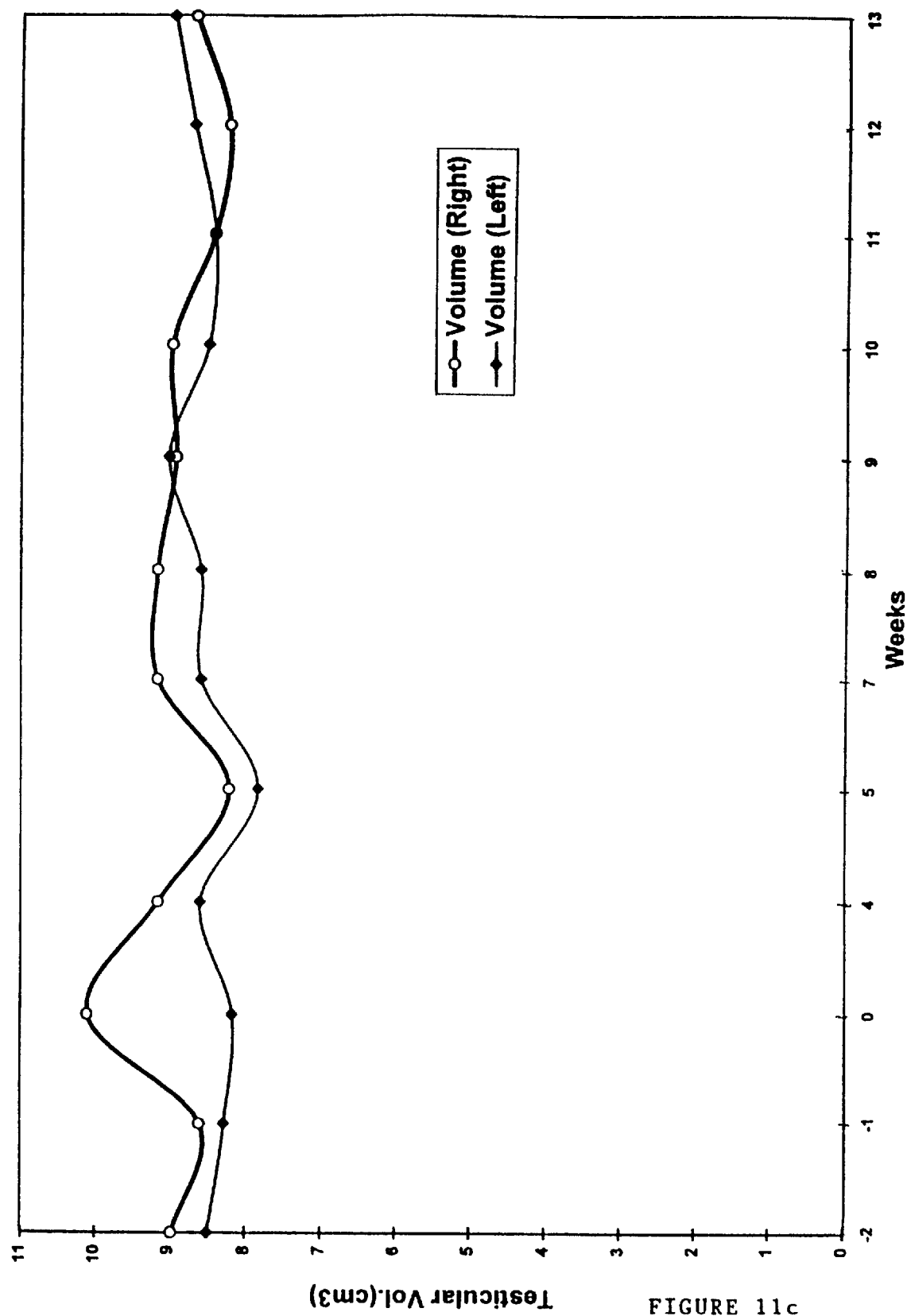

FIG. 11: Provide graphical results of testicular size data from a controlled dog, up to nine weeks post implantation with a placebo (i.e. identical formulation II less deslorelin).

Figure 12:
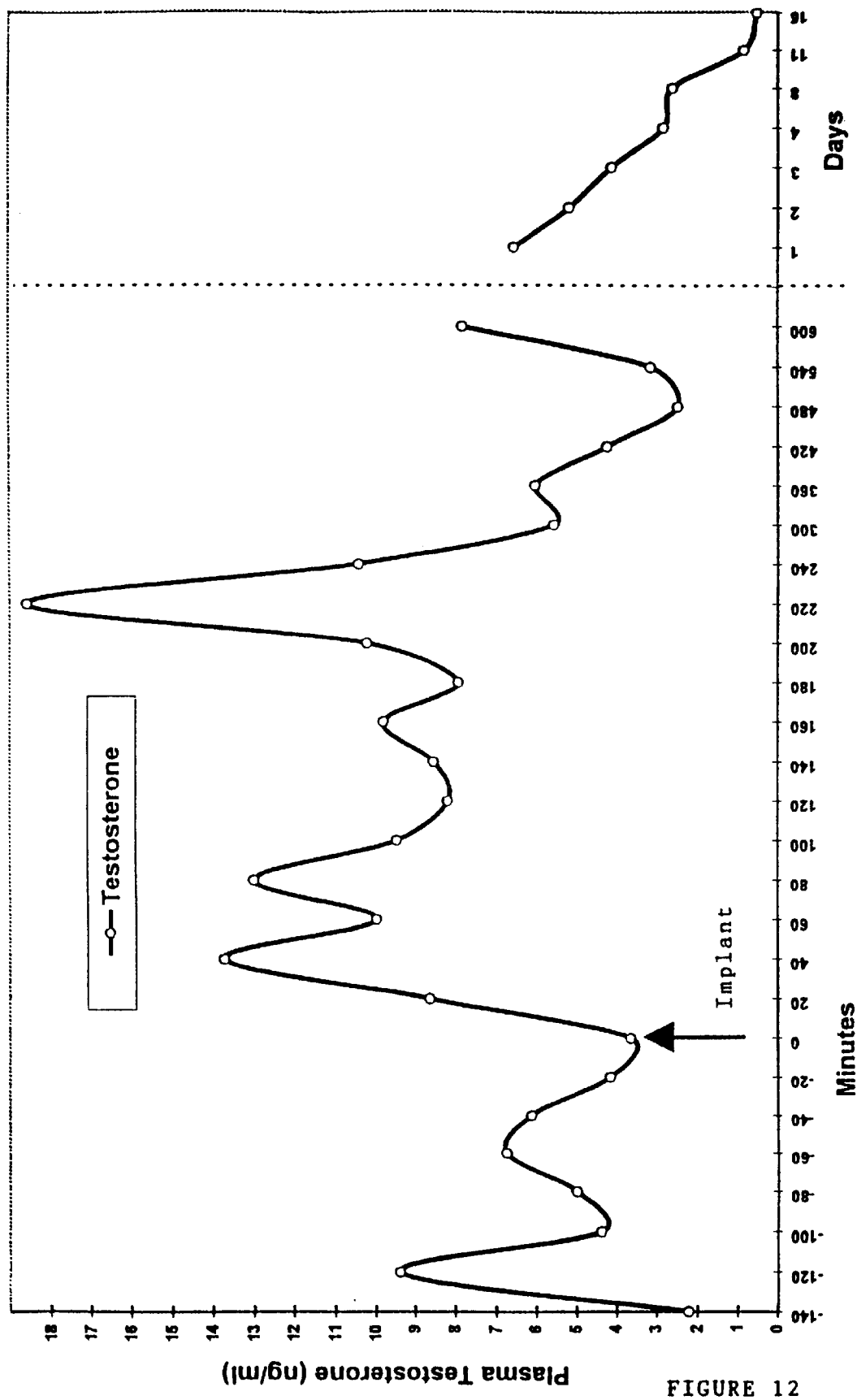
Figure 13:
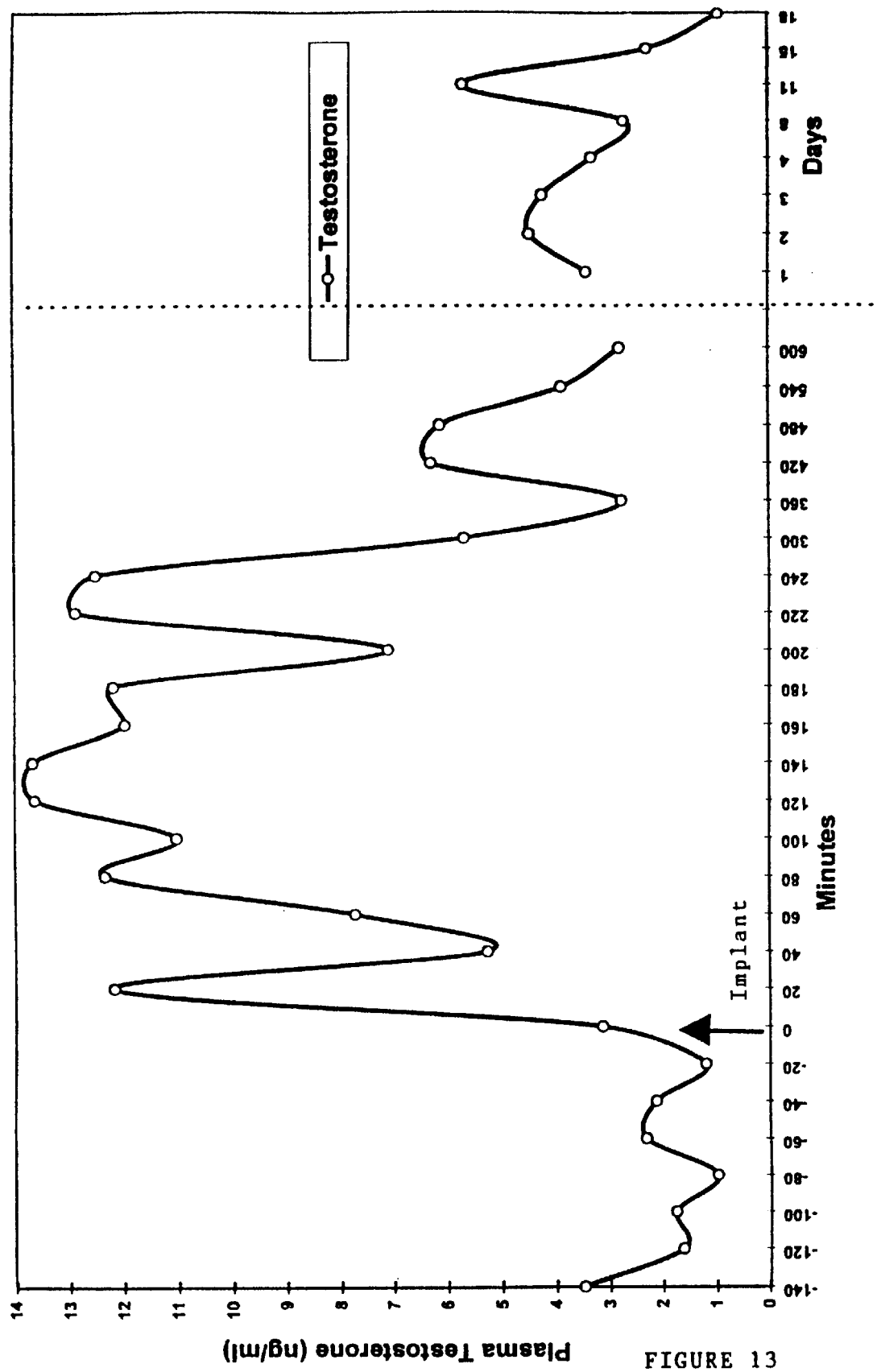

FIG. 12 and 13: Provides graphical results of plasma testosterone levels from dogs implanted with the deslorelin formulation. These dogs were euthanased after it was observed that the formulation was active, in order to collect tissues.

EXAMPLE 1

Dog Contraceptive Formulation I

A formulation comprising 94% stearin, 5% deslorelin (on an active basis) and 1% lecithin was evaluated in dogs. This formulation was produced as follows:

Stearin (supplied as free flowing beads of 1 mm or less in diameter made by Vandenberg Foods) and lecithin (supplied as a deep brown viscous syrup from R. P. Schearer) were hand mixed using a spatula in a small beaker. The deslorelin was then added and thoroughly mixed into the excipients. The mixed material was transferred to the barrel of a ram extruder that has a 1 mm nozzle attached and is equilibrated to 55° C. The ram extrusion pressure is 40 psi. The ram was attached and pressure applied until the product began to extrude. At this point the pressure was backed off and the product allowed to reach 55° C. The product was then extruded—3 g over a 30 second period. The resulting exudate was allowed to cool and then broken up and re-extruded through a 1 mm nozzle. This step was included to ensure uniformity of content throughout the matrix. The 1 mm nozzle was then replaced with a 2.3 mm diameter nozzle. The same product temperature equilibration procedure was conducted prior to extrusion. The product was then extruded and after cooling the long rods produced could be sectioned into lengths of the required weight.

The rods produced were implanted into male dogs using standard techniques. Results obtained demonstrated that the release of deslorelin from the rods in vitro followed a reproducible path and continued for up to 250 days. In the dogs a continued decline in testicular size was seen for at least 5 months and suppression of plasma testosterone levels for at least 4 months were observed.

Figure 1:
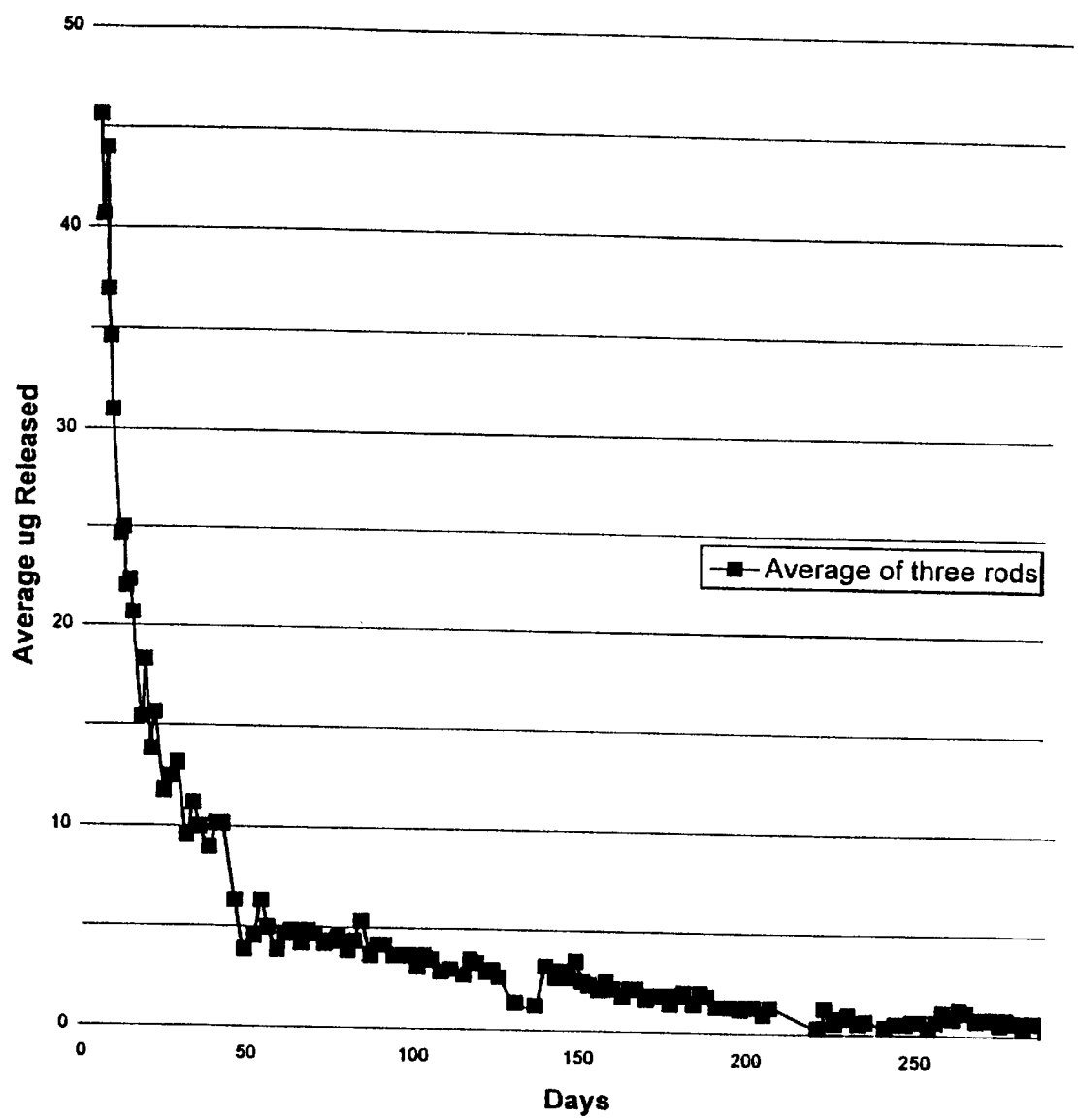
FIG. 1: Provides a graph showing the average daily in vitro release profile from three 60 mg rods of formulation I, demonstrating an initial rapid release of the agent and then continued release extending over a prolonged period.
Figure 2:
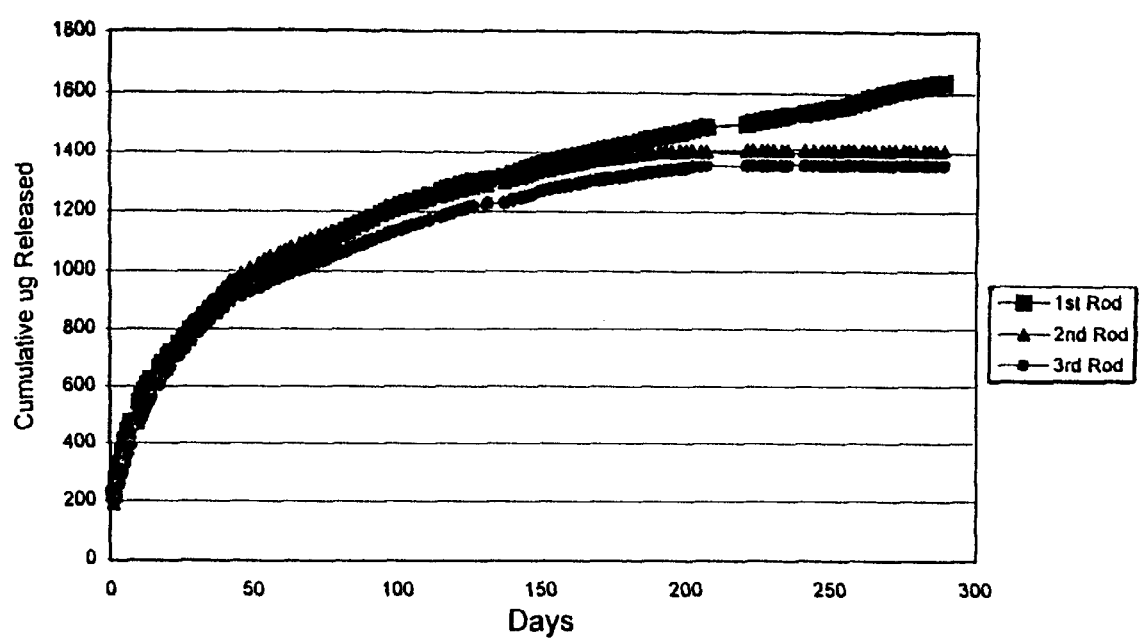
FIG. 2: Provides a graph showing the cumulative in vitro release profile from three 60 mg rods of formulation I, demonstrating the reproducible release observed, extending for at least 250 days.
Figure 3:
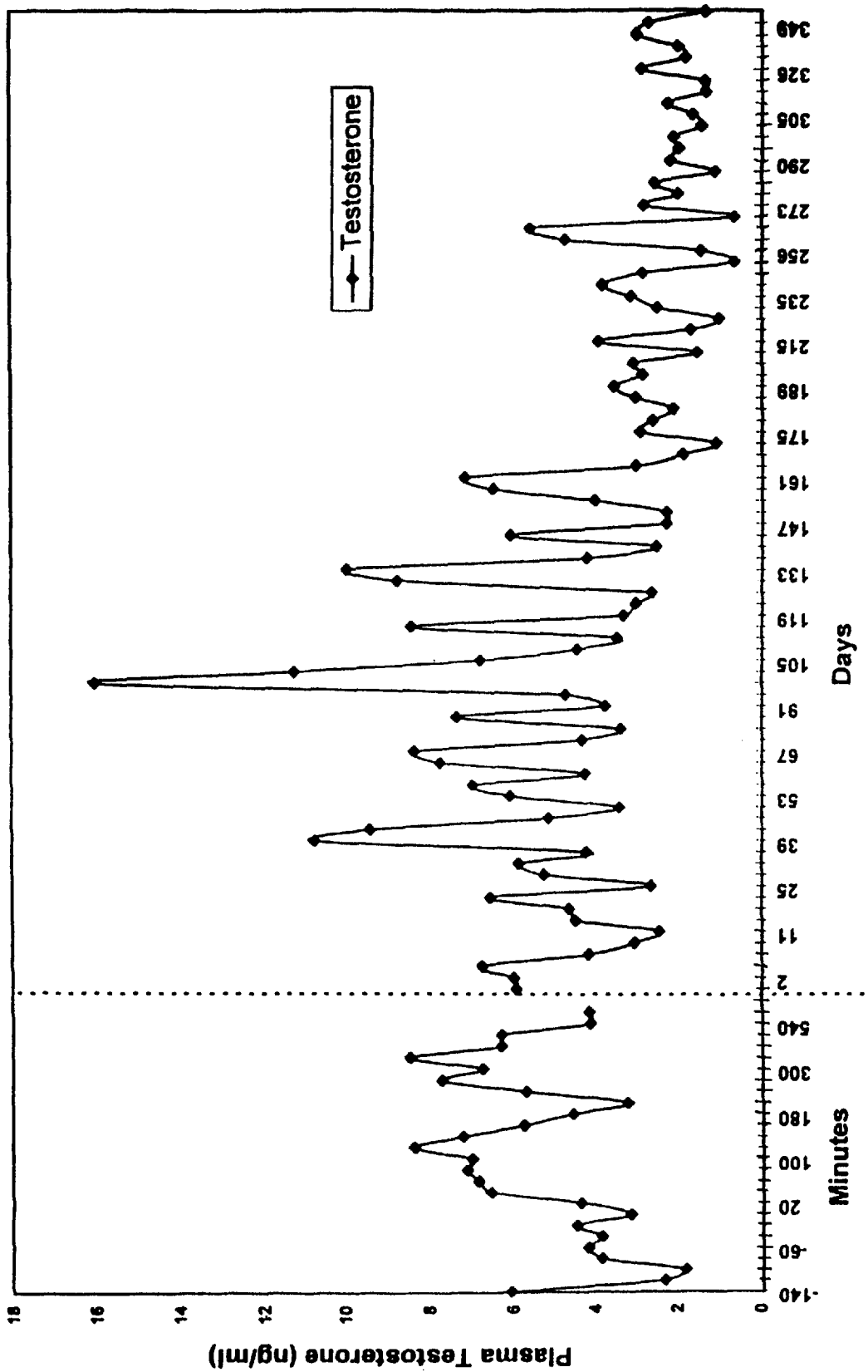
FIG. 3: Provides graphical results of normal plasma testosterone levels in a control dog.
Figure 4:
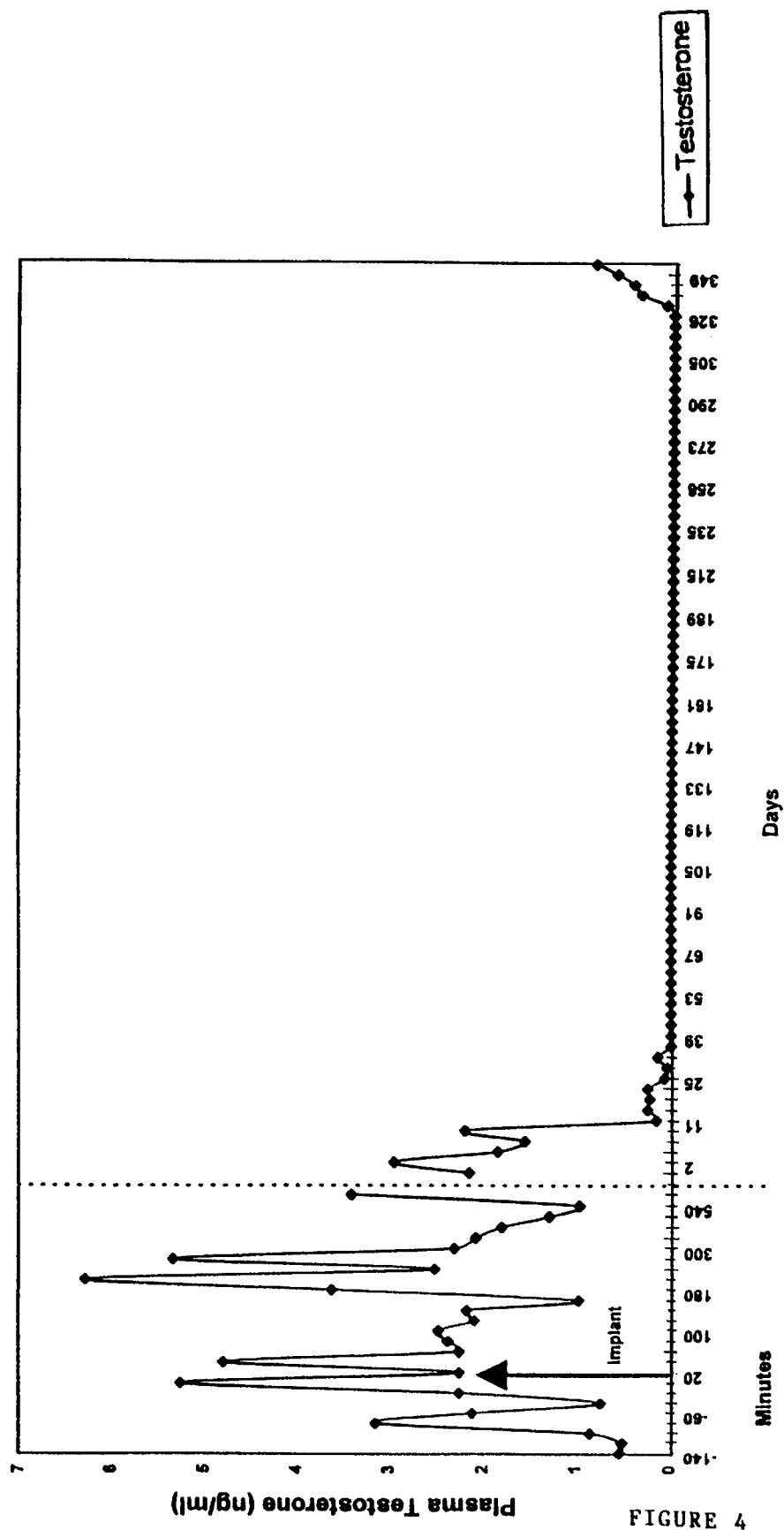
FIGS. 4–7: Show.
Figure 5:
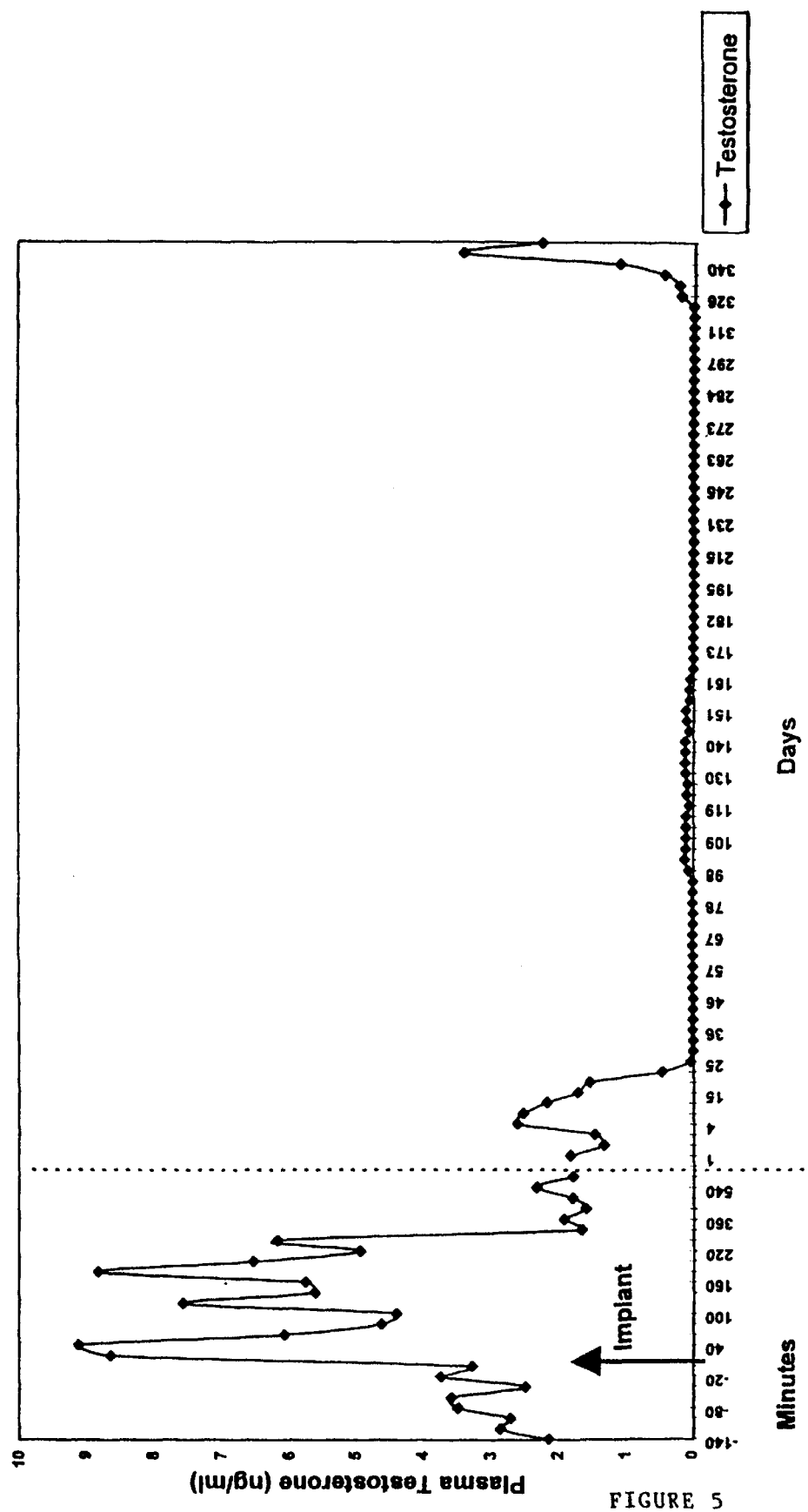
Figure 6:
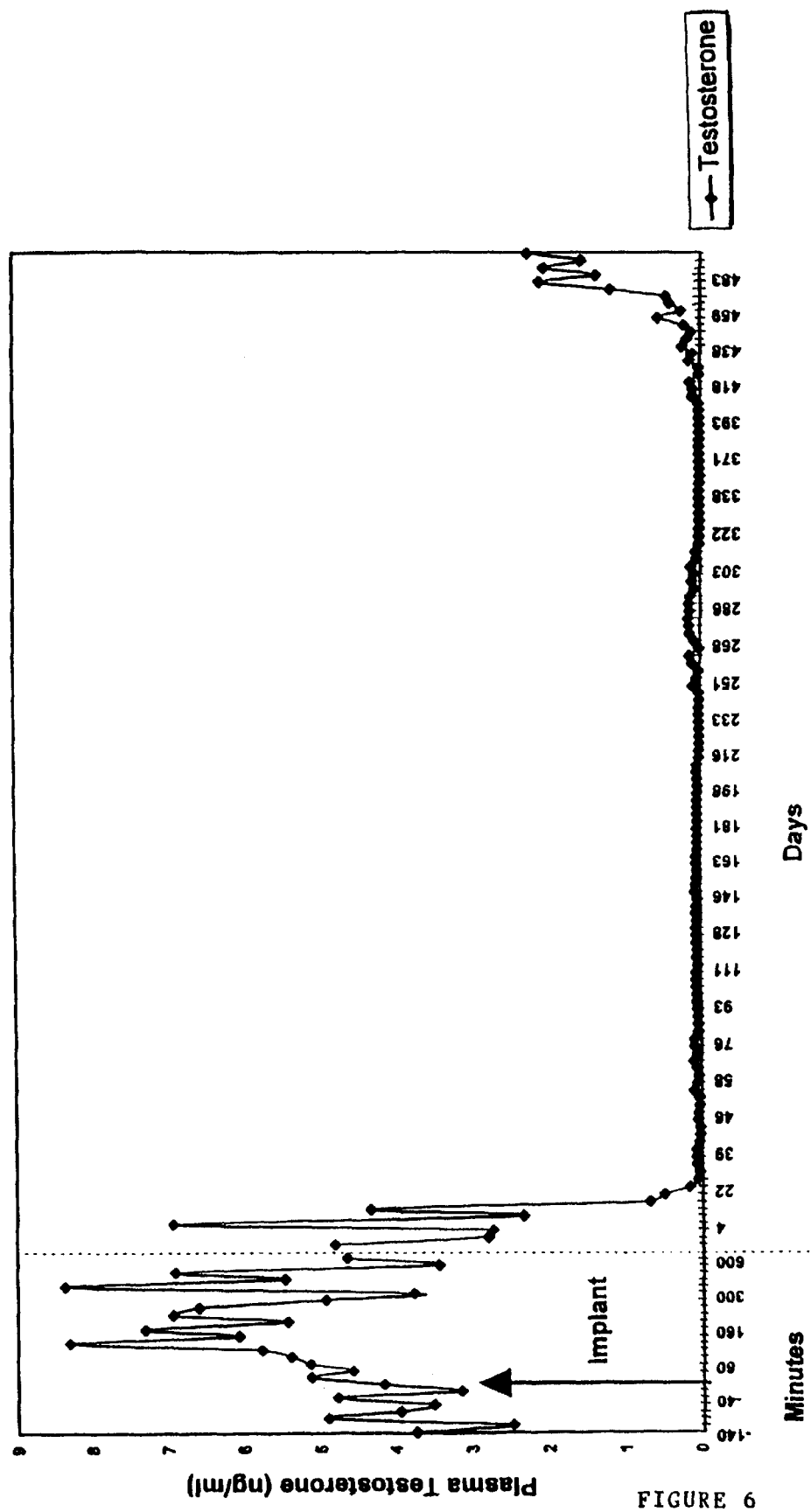
Figure 7:
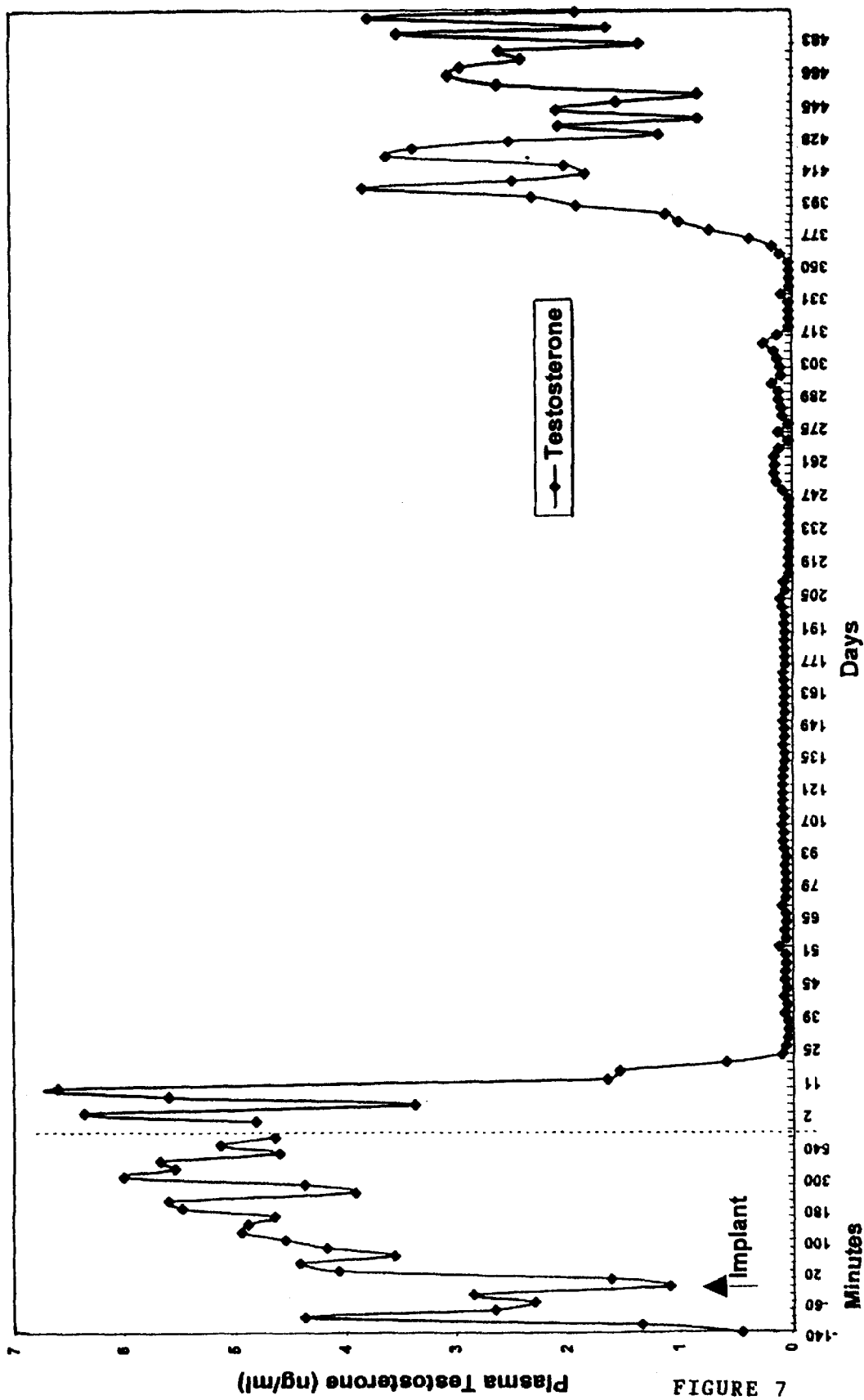

FIGS. 1 and 2 provide results of in vitro deslorelin release with 60 mg rods. The assay involved immersing the rod into a container with 1 ml of phosphate buffered saline (prepared as described below) which is placed in a reciprocating water bath at 37° C. The saline is replaced daily and the withdrawn saline assayed for deslorelin with HPLC.

Phosphate buffered saline (PBS—pH 7.3) referred to herein, is prepared by dissolving 8.00 g of sodium chloride, 100 g g di-sodium hydrogen phosphate anhydrous, 0.40 g sodium dihydrogen phosphate dihydrate (0.31 g if anhydrous), and 0.05 g sodium azide in 1 liter of deionised water.

EXAMPLE 2

Dog Contraceptive Formulation II

A formulation comprising 93% stearin, 5% deslorelin (on an active level) and 2% lecithin was evaluated in dogs. This formulation was produced as follows:

Stearin beads (ADMUL PO 58 from Quest International Australasia Limited) and lecithin (Topcithin 300, Bronson & Jacobs, Australia) were hand mixed using a spatula in a small beaker. The deslorelin was then added and thoroughly mixed into the excipients. The material was transferred to the barrel of a ram extruder that has a 1 mm nozzle attached and is equilibrated to 55.8° C. The ram extrusion pressure is 40 psi. The ram was then attached and pressure applied until the product began to extrude. At this point the pressure was backed off and the product allowed to reach 55.8° C. The product was then extruded—3 g over a 30 second period. The resulting extrudate was allowed to cool and then broken up before re-extruding the mixed granulation through the 1 mm nozzle at 58.3° C. and into an injectable mould that generates a finished rod product that is 2.3 mm in diameter and approximately 25 mm long. The rods are then sterilised by gamma irradiation.

The rods produced were implanted into male and female dogs (0.5, 1 or 2×120 mg rod containing 6 mg of deslorelin). The results obtained with the dogs are set out in FIGS. 9 to 19 and Tables 1 to 4. The results show that the formulation is able to suppress testosterone levels in dogs for 12 months or more and in bitches for at least 5 months. Accordingly, the formulation of the present invention is able to prevent reproductive function in dogs over an extended period of time.

TABLE 1

| Progesterone positive bitches - non pregnant | | |
|---|---|---|
| Dogs | Implanted | Observation (after 1 month) |
| BA1/6 | May 1996 | No post treatment oestrus |
| BA2/6 | May 1996 | No post treatment oestrus |
| BA3/6 | May 1996 | No post treatment oestrus |
| PW1/6 | May 1996 | Mild oestrus display Progesterone low |
| PW4/12 | May 1996 | Progesterone dropped by treatment |

Results for this group of 5 bitches demonstrate rapid suppression of reproductive function and of plasma sex hormone levels over the first few weeks post implantation.

TABLE 2

| Progesterone positive bitches - pregnant | | |
|---|---|---|
| Dogs | Implanted | Observation (after 0.5 to 1 months) |
| BA1/61 | June 1996 | No oestrus |
| PW1/12 | May 1996 | No oestrus |

These are controls in pregnant bitches.

TABLE 3

| Progesterone positive bitches | | |
|---|---|---|
| Dogs | Implanted | Observation (after 2 to 5 months) |
| BB1/6 | January 1996 | Display of oestrus then no activity |
| BB2/6 | February 1996 | Display of oestrus then no activity |
| BB3/6 | February 1996 | Display of oestrus then no activity |
| BB4/6 | March 1996 | Display of oestrus then no activity |
| BB1/31 | April 1996 | Display of oestrus then no activity |
| BB1/61 | April 1996 | Prolonged oestrus |

Results for this group of 5 bitches show that reproductive behaviour and plasma hormone levels (not shown) can be suppressed for at least 5 months following implantation.

TABLE 4

| Implant Safety in dogs | | |
|---|---|---|
| Dog No. | Histology, at Implant Site | Return to Fertility (after 12 months) |
| Dog 46 | No cellular changes detected | Yes |
| Dog 79 | No cellular changes detected | Yes |
| Dog 40 | No tissue taken | Yes |
| Dog 47 | No tissue taken | Yes |

These results show no negative pathological changes at the implantation site and return to fertility of 4 dogs implanted with deslorelin implants for 12 months.

We claim:

1. A pharmaceutical or veterinary formulation comprising about 2–10% deslorelin, about 0.5–2.5% lecithin and about 85–97.5% stearin, wherein the formulation releases, in vitro, deslorelin into phosphate buffered saline at 37° C. at a rate of about 2–80 µg/day for at least 200 days, said phosphate buffered saline being prepared by dissolving 8.00 g of sodium chloride, 1.00 g di-sodium hydrogen phosphate anhydrous, 0.40 g sodium dihydrogen phosphate dihydrate and 0.05 g sodium azide in one liter of deionized water.

2. A formulation according to claim 1, wherein the formulation comprises about 5–10% deslorelin, about 0.5–1.5% lecithin and about 89–94% stearin.

3. A formulation according to claim 1, wherein the formulation comprises about 5% deslorelin, 1% lecithin and 94% stearin.

4. A formulation according to claim 1, wherein the formulation comprises about 5% deslorelin, 2% lecithin and 93% stearin.

5. A method of preventing reproductive function in an animal for at least 3 months, the method comprising administering to the animal a formulation according to claim 1.

6. A method of treating a disease or condition in an animal by suppressing sex hormone levels, the method comprising administering to the animal a formulation according to claim 1.

7. A method according to claim 6, wherein levels of testosterone or estradiol are suppressed.

8. A method according to claim 6 or 7, wherein the disease or condition is selected from prostate cancer, ovarian and breast cancer, endometriosis, myoma and premenstrual tension, and precocious puberty.

9. A formulation according to claim 1, wherein 0.31 g of sodium dihydrogen phosphate in anhydrous form is used to form said phosphate buffered saline.

\* \* \* \* \*